United States Patent [19]

Mayeaux

[11] 4,142,860
[45] Mar. 6, 1979

[54] APPARATUS FOR PRODUCING A CALIBRATION SAMPLE FOR ANALYTICAL INSTRUMENTATION

[76] Inventor: Donald P. Mayeaux, Rte. 3, Box 2914, Prairieville, La. 70769

[21] Appl. No.: 698,883

[22] Filed: Jun. 23, 1976

[51] Int. Cl.² .................. B01F 13/08; C09K 3/00; G01C 25/00; G01N 31/00
[52] U.S. Cl. .................. 137/557; 23/232 R; 73/1 G; 252/408; 366/273; 137/565; 137/604; 422/119
[58] Field of Search ........ 23/232 R, 254 R, 285 (U.S. only), 23/259, 254 E; 73/1 G; 259/146, 147, 148, 151, 153, DIG. 46; 141/61

[56] References Cited

U.S. PATENT DOCUMENTS

| | | | |
|---|---|---|---|
| 1,272,922 | 7/1918 | Davis et al. | 23/232 R |
| 2,578,002 | 12/1951 | Fryer | 23/285 X |
| 2,642,418 | 6/1953 | Wenning | 23/285 UX |
| 2,875,220 | 2/1959 | Bremer, Jr. | 23/285 X |
| 3,071,447 | 1/1963 | Bernhardi | 23/285 UX |
| 3,248,413 | 4/1966 | Motl | 23/285X |
| 3,520,657 | 7/1970 | Frumerman | 23/232 R X |
| 3,528,779 | 9/1970 | Fontijn | 23/254 E X |
| 3,841,835 | 10/1974 | Kishimoto et al. | 23/254 R X |
| 3,897,682 | 8/1975 | Brooks | 73/406 X |
| 3,900,186 | 8/1975 | Balas | 259/DIG. 46 X |
| 3,911,723 | 10/1975 | Ritter | 73/1 G |

*Primary Examiner*—Joseph Scovronek
*Attorney, Agent, or Firm*—L. A. Proctor

[57] ABSTRACT

Apparatus for and method of preparing reference mixture gas samples for use with analytical instrumentation and small scale chemical reactions and processes, having a motor-driven magnetic stirrer with the motor and driving magnet mounted externally of the mixing chamber. Such structure together with the mass of the mixing chamber, which is large in comparison to the mass of the samples, helps to stabilize the temperature of the mixing chamber.

9 Claims, 2 Drawing Figures

APPARATUS FOR PRODUCING A CALIBRATION SAMPLE FOR ANALYTICAL INSTRUMENTATION

BACKGROUND OF THE INVENTION

This invention relates to the field of preparing accurate gaseous and/or vapor mixtures for analytical instrumentation. Gas mixtures are in widespread use as calibration or reference standards for analytical instrumentation and as feed stock for scaled down chemical reaction or processes particularly in research and development.

Commercial bottled gas and vapor mixtures are available from numerous suppliers for analytical instrumentation use. However, the occasion often arises when it is of advantage to the user to have apparatus capable of mixing gases and/or vapors accurately to predetermined proportions.

Examples of these occasions are as follows:

1. One lacks the time required to obtain a commercially prepared mixture (a minimum of twenty-four hours is generally required although one to two weeks is commonly accepted delivery time);
2. The chemical stability or reactiveness of components in the mixture dictates that it be utilized immediately after preparation;
3. The accuracy of commercial mixtures is in question;
4. Sufficiently accurate mixtures are not easily obtained;
5. The selection of a final mixture requires a "trial and error" procedure by the user;
6. Only small quantities are required; and
7. The components of a mixture tend to stratify (heating and extensive rolling of the vessel are presently the only means for maintaining a homogeneous mixture of components which are easily stratified).

Preparation of gaseous or vapor mixtures by the user is limited to a few devices utilizing mass flow and permeation techniques. These are dynamic devices with blending occurring only when components are flowing. These techniques are not accurate and lend themselves to applications requiring few components in the mixture. Some of the devices can only be applied for specific mixtures. An example of this technique is disclosed in U.S. Pat. No. 3,948,281.

Commercial preparation of gaseous or vapor mixtures falls in two general categories. One is a gravimetric technique in which the vessel and its contents are weighed and the other is a partial pressure technique. The accuracy of the gravimetric method is dependent to a large degree on the weight of each component relative to the total weight of the vessel and its contents. This results in lower accuracies being attained in low density mixtures, such as hydrogen and helium, and also in situations where the components of interest are in low concentration.

The partial pressure method has limited accuracy due to use of high pressures required to make the process commercially feasible, lack of suitable means for homogenizing the mixture, and absence of temperature control. High pressures produce large compressibility factors which are not predictable with any degree of accuracy, being dependent on the composition and state of intermediate and final mixtures.

Lack of homogenizing capability and temperature control results in large errors due to variations in temperature during the vessel filling process which are caused by decompression and compression of gases. The partial pressure technique, as has been practiced commercially and by end users, is not a suitable method for the preparation of accurate gas or vapor mixtures. It is best used for preparing "target" concentrations, followed by analysis, or for blending low grades of calibration gases. Reference is made to the 1975 copyrighted book *Gas Mixtures — Facts and Fables,* by Frank Scarporoicer that is available from Matheson Gas Products Company, 932 Paterson Plank Road, P.O. Box 85, East Rutherford, New Jersey 07073 and which is hereby incorporated by reference for all purposes herein.

Very low concentrations of gaseous or vapor mixtures are also difficult to prepare accurately and often require elaborate procedures, some of which are suitable only for specific compounds. An example is gas permeation, which is a dynamic technique, requires precision temperature control, has a limit on active component life, and has a narrow range of applicability.

In general, both high and low gas or vapor mixtures have previously required both a preparation procedure followed by an analysis procedure to confirm composition of the mixture.

Widespread use of analytical instruments such as gas chromatography apparatus now exists in the chemical process industry as well as in other fields. For example, see U.S. Pat. No. 3,595,063 to Loew as well as U.S. Pat. No. 3,888,109 to Sharki for a support system increasing the capability of a gas chromatograph. Such gas chromatographs are capable of rapidly analysing and indicating the presence of the mixture components in a gas sample both qualitatively and quantitatively. Since gas chromatographs enables a process operator to quickly determine the composition of a sample, more frequent analyses of the various process stream are available for enhancing process efficiency.

One major drawback to the many advantages of the use of gas chromatographs apparatus has been the need for a reference or calibration sample by which the gas chromatograph apparatus is both calibrated and from time to time tested for accuracy. Such reference samples have previously been prepared by chemists working in the laboratory using the techniques set forth above.

Gas blenders are known as evidenced by U.S. Pat. No. 2,950,618 to Lewis. Furthermore, systems have been developed for determining the concentration of a gas in a mixture, such as disclosed in U.S. Pat. No. 2,817,350 to Bradner, et al. Also, as disclosed in U.S. Pat. No. 3,817,085, polarographic sensors or electrolytic sensors may be used to measure the partial pressure of a component in a mixture.

SUMMARY OF THE INVENTION

This invention relates to a new and improved method and apparatus for providing a calibration sample for analytical instrumentation.

The apparatus includes a mixing chamber in which the components are blended while an absolute pressure transducer monitors the absolute pressure in the chamber. Suitable inlet valving is provided as well as a vacuum system for exhausting the chamber as desired. A magnetic stirrer means is provided for homogenizing the mixture of gases in the chamber.

By controlling the pressure increase during the introduction of each component into the mixture the concentration of each gas component in the mixture is controlled.

This invention relates to a new and improved method and apparatus for the preparation of multicomponent gaseous and vapor mixtures in low and high concentrations with a degree of accuracy which negates the requirement for analysis to ascertain the composition of the final mixture. The apparatus also serves as a storage facility for the mixture produced and has provisions for transfer of its contents to a separate vessel or for direct use.

The invention will be used primarily in the area of analytical instrumentation which requires accurate gas and vapor mixtures for reference or calibration.

It is to be understood that the reference samples prepared by the method and apparatus of the present invention will be disclosed in the context of gas chromatographs, but such reference samples are equally well adapted for other purposes and other analytical instruments.

An object of the present invention is to provide a new and improved apparatus for preparing calibration samples for gas chromatography.

Another object of the present invention is to provide a new and improved method for preparing calibration samples for gas chromatography.

DESCRIPTION OF THE PREFERRED EMBODIMENT

Figure 1:
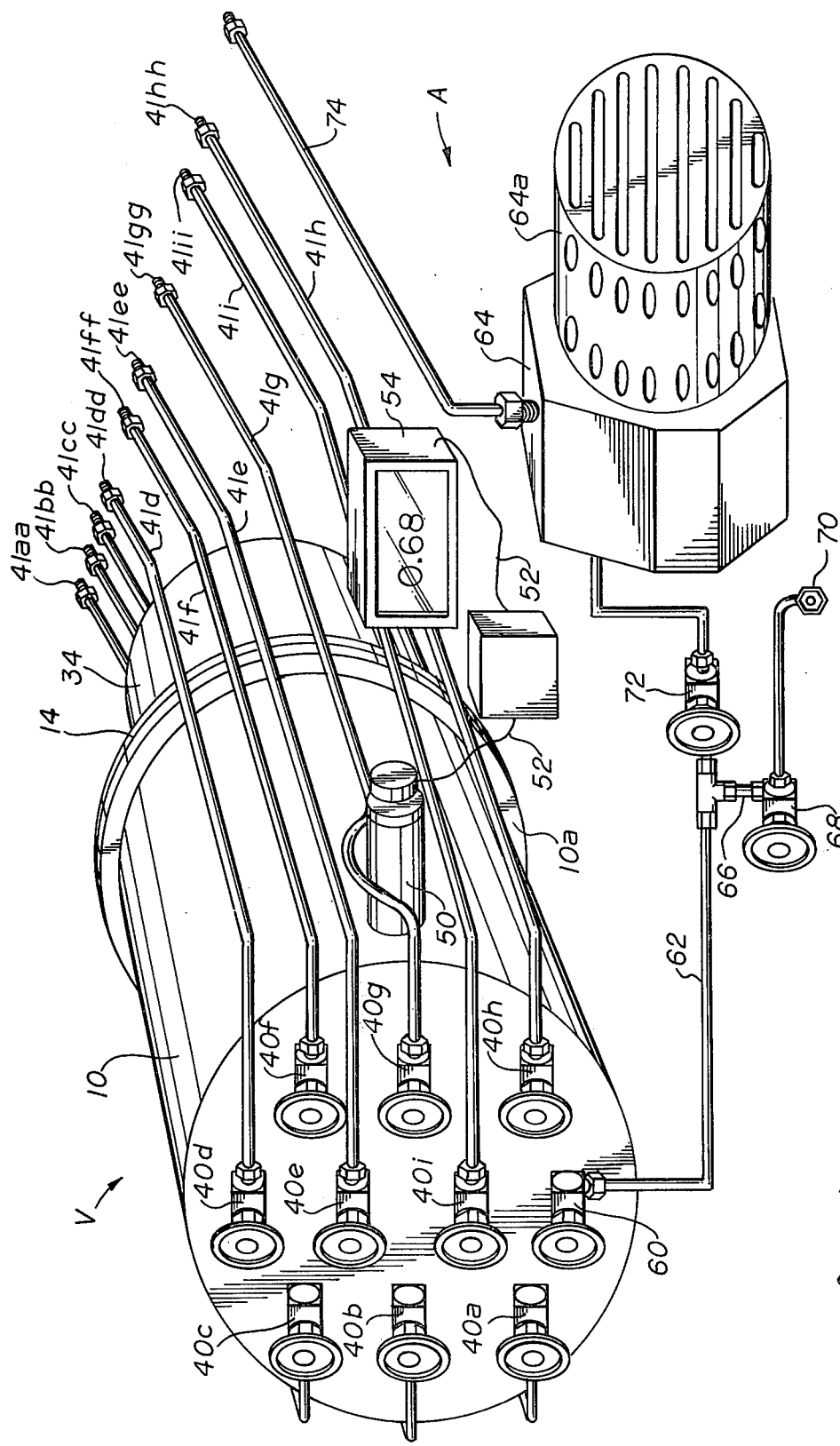
FIG. 1 is an isometric view of the calibrated sample blender apparatus of the present invention.

The gas blending apparatus of the present invention is schematically illustrated in FIG. 1. The gas mixture blending apparatus, generally designated A, is used to prepare reference or calibration samples for use with gas or vapor analyzers (i.e., gas chromatographs, spectrophotometers, etc.). The reference samples are used to both calibrate and to check the analyzers for accuracy.

The apparatus A includes a pressure vessel, generally designated V, having a body 10 that is preferably formed from a twelve inch length of schedule 10S or 5S stainless steel Type 304 pipe and being approximately twelve inches in diameter. The pressure vessel V further includes end caps 12 and 14. The end cap 12 is preferably secured to the vessel body 10 at the periphery by welding while end cap 14 is preferably attached with suitable bolting (not illustrated) to flange 10a of the vessel body 10 in the usual manner. The end caps 12 and 14 are preferably constructed of Type 304 stainless steel plate suitably cut and drilled. The mass of the vessel V will provide a sufficient heat sink to hold the gas temperature substantially stable during the gas blending process. With the preferred construction of the vessel V, a cylindrical mixing member 16 is formed by the pressure vessel V of approximately twenty liters, but other dimensions and shapes of mixing chambers may be utilized.

Figure 2:
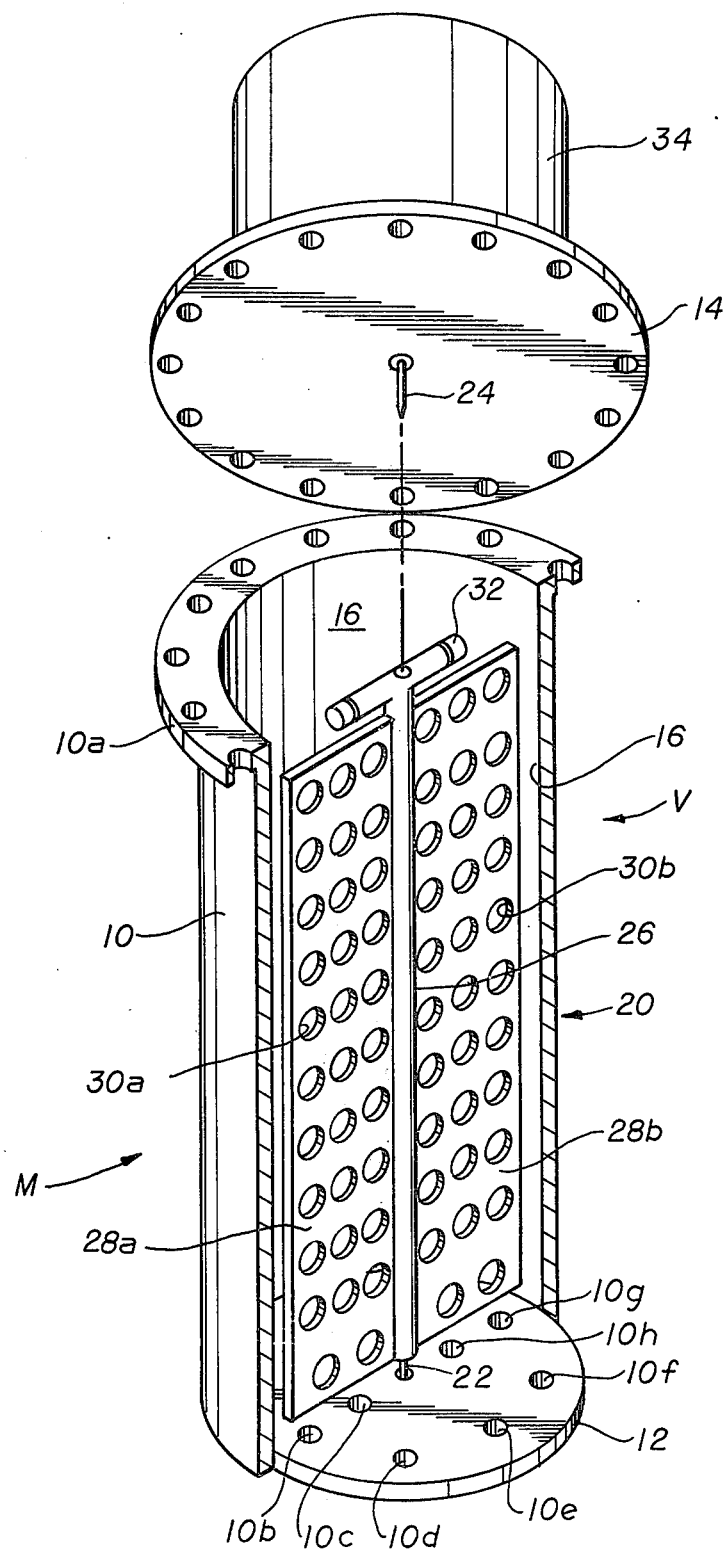
FIG. 2 is an exploded cut-away of the pressure vessel detailing the assembly of the magnetic mixer.

As best illustrated in FIG. 2, a mixing or stirring means is generally designated M. The mixer M includes a stirrer or paddle means 20 that is disposed within the mixing chamber 16 and rotatably supported on journal pins 22 and 24 which are in turn fixed to the end plates 12 and 14, respectively. The paddle means 20 is preferably formed with a longitudinally extending central shaft 26 which is concentrically rotationally mounted on the journal pins 22 and 24. Secured to the central shaft 26 are stirrer blades 28a and 28b and which are circumferentially spaced 180° apart on the shaft 26. While two paddle blades 28a and 28b are illustrated, it is to be understood that variations in the number and form of the blades 28a and 28b will be readily apparent to those skilled in the art. Also, the arrangement of the opening or perforations indicated at 30a and 30b in the plates 28a and 28b, respectively, as well as the number of the perforations will be apparent to those skilled in the art.

Mounted on the central shaft 26 adjacent the end cap 14 is a rod or bar 32 which is made of corrosion resistant magnetic material. The bar magnet 32 provides the magnetic field drive linkage for rotating the shaft 26 and the attached paddle blades 28a and 28b. The flange connection between the vessel body 10 and the end plate 14 permits access to the chamber 16 for installation and to perform maintenance work on the paddle means 20.

Secured to the end plate 14 on the opposite side from the pivot pin 24 is a mixer means motor housing 34. Disposed within the housing 34 is an electrical motor (not illustrated) producing a rotating shaft speed of approximately 40 to 50 revolutions per minute and which carries a magnet similar to the magnet bar 32 on the paddle 20. The motor magnet is disposed adjacent the end plate 14 when positioned in the housing 34 in order that the movement of the magnetic field of the motor driven magnet in the housing 34 will effect rotation of the magnet 32 located in the mixing chamber 16 to rotate the paddle means 20 to homogenize the gas mixture in the chamber 16.

A plurality of openings, referenced as 10b through 10h in FIG. 2, are preferably formed in the end cap 12 for the introduction of the component gases into the mixing chamber 16. Preferably, the openings 10b–10h are threaded in order that right angle inlet control valves for the individual component gases may be attached directly to the end plate 12 as illustrated in FIG. 1. The right angle type valves, generally designated 40a–40i, are preferred because they allow designing for a minimum of volume between the valve seat and the chamber 16 that is not agitated by the paddles 28a and 28b in homogenizing the gas mixture in the chamber 16. Each of the inlet control valves 40a–40i are provided with the usual rotating operating handle, designated 40a'–40i' respectively, for opening and closing each inlet valve in the usual manner. The valve 40a is also connected through conduit 41a with a source (not illustrated) of a particular desired gas component for the mixture. The supply of component gas are normally bottled gases of certified purity and the conduit 41a may be connected directly to the pressure regulator on the cylinder of the component gas as is well known. Frequently, for safety, a bulkhead is provided between the cylinders of bottled gases and the equipment utilizing the bottled gases. FIG. 1 illustrates such a bulkhead arrangement, but it is to be understood that the end of the conduit 41a to 41aa is to be connected in the usual manner with the pressure regulator of a high pressure cylinder of a desired component gas. Conduits 41b through 41h are connected in such manner also.

Mounted directly on the pressure vessel body 10 is an electrical absolute pressure transducer or other suitable means 50 for continuously monitoring the absolute pressure accurately within the mixing chamber 16. The transducer 50 is mounted directly with the pressure vessel body 10 to minimize the dead area between the pressure sensor of the transducer 50 and the mixing chamber 16. In the preferred embodiment, a Model 1332-A-6 transducer manufactured by Rosemount, Inc., P.O. Box 35129, Minneapolis, Minnesota 55435, is utilized. In addition, reference may be made to U.S. Pat. Nos. 3,195,028; 3,271,669; and 3,318,153 for additional disclosure on the operation of such pressure transducers and the aforementioned three patents are hereby incorporated by reference for all purposes. Preferably, the output of the transducer which in the preferred embodiment is a high level DC output voltage or current linear with pressure that is electrically communicated through wires 52 to a voltmeter 54 which preferably displays the output in the illustrated digital form.

Disposed within an opening similar to that of 10b in the end plate 12, is a vent opening (not illustrated) which preferably has threadedly mounted therein a right angle type vent or exhaust valve 60. The vent valve 60 is in turn connected to the vacuum conduit system or means 62 which in turn communicates with the vacuum pump means 64. The vacuum conduit means 62 further includes a branch or sample connection 66 having a sample valve 68 therein which controls flow through the branch connection 66. The sample connection 66 is provided with suitable means, such as the threaded connector indicated at 70, to which sample containers or bombs may be attached in order that the reference gas mixture blended in the chamber 16 may be transferred. It is to be understood that such sample container or bombs and their operation and use are well known to those skilled in the art. The pressure differential between the gas mixture in the chamber 16 and in the sample container will of course be sufficient to move a portion of the referenced mixture into the sample bomb which may be disconnected from the connector 70 and stored or taken directly to the gas analyzer for calibration or testing purposes.

Disposed in the vent conduit 62 between the branch connections 66 and the vacuum pump 64 is a block valve 72 for controlling flow through the vent conduit 62. Normally, the valve 72 is closed when transferring a sample from the mixing chamber 16 through the valve 68 into the sample bomb.

Disposed within an opening similar to that of 10b in the end plate 12 may be an opening (not illustrated) which preferably has threadedly mounted therein a septum inlet to accommodate the injection of gases, vapors, or liquids into the mixing chamber by means of a syringe (not illustrated). It is to be understood that such septum inlets and their use with injection syringes for introducing small, but critical components, in the sample are well known to those of ordinary skill in the art.

The vacuum pump means 64 may be of any suitable type but preferably the "Vac Torr" Model DD-20 vacuum pump manufactured by Fisher Scientific Company of 711 Fourth Avenue, Pittsburgh, Pennsylvania 15219, is employed. The preferred model has an integral electric motor 64a, but it is understood that separate motor pumps may be employed when suitably coupled. The output of the pump 64 is preferably communicated through discharge conduit 74 to the bulkhead or other remote location for safety reasons.

OPERATION

The apparatus and method are based on the application of partial pressure and "addition of specific volume" technique singularly or in combination. The partial pressure technique is employed by controlling the pressure increase during the introduction of each component into the mixture which determines its concentration. The "addition of specific volume" technique is the direct introduction of a known quantity of liquid, vapor, or gas into the mixing chamber by means of a syringe. The other major components of the mixture are introduced by appropriate valving which will be described further.

Since the invention is intended for use primarily by the user of gas or vapor mixtures it is not necessary to utilize high pressures. The apparatus is designed for low pressures (approximately 100 psia or less). At low pressures the error due to compressibility is minimal. The mixing chamber pressure is monitored with a device which provides an accurate indication of the relationship of component volumes on the basis of their partial pressure.

The apparatus includes a provision for homogenizing the gas mixture with a magnetic stirring device. This eliminates errors due to stratifying and also aids in rapid stabilizing of the gas temperature.

The temperature of the mixing chamber and its contents is stabilized by the use of a chamber mass which is large relative to the mass of its contents.

The chamber has multiple valving to facilitate the introduction of individual gaseous components without cross-contamination.

A septum inlet is mounted on the chamber to allow syringe injection for the "addition by specific volume" technique. This feature is utilized for the preparation of very low (parts per million range) concentrations of vapor or gas. The exact concentrations are calculated on the basis of the mixing chamber volume, the volume of gas or vapor introduced by syringe and the system temperature and pressure. When liquid is injected directly the vapor volume is calculated based on Avogadro's law and the concentration determined in a similar manner as for direct injection of gas or vapors.

The apparatus also includes a vacuum pump for exhausting the chamber or a separate storage vessel.

The partial pressure and/or "addition by specific volume" techniques may also be utilized to add components to an existing gaseous or vapor mixture, increase the concentration of any of its components, or dilute it to any degree.

In the use and operation of the present invention, the apparatus A is assembled in the manner illustrated and the inlet conduits 41aa-41hh are connected to the pressure regulators on the cylinders containing the desired gas components to be blended. The vent valve 60 is placed in the open position while all of the inlet valves 40a-40i are placed in the closed position. The vacuum conduit valve 72 is placed in the open position while the branch valve 68 is closed. The vacuum pump 64 is then turned on to reduce the pressure in the chamber 16.

With the vacuum pump 64 operating, each of the inlet valves is in turn opened to purge the corresponding inlet conduit of any impurities that may be present in that conduit. For example, the valve 40a is open for sufficient periods to purge the conduit 41a of air and other matter that may be present therein when the end 41aa is connected to the bottle of component gas. After this operation is complete, the flow of pure gases into the chamber 16 can be controlled with the valves 40a-40i at the pressure vessel V. The above operation needs only to be repeated whenever it is necessary to change out a cylinder of component gas or to change components.

PREPARATION OF A FINISHED MIXTURE

With the valves 40a–40i in the closed position, the vacuum pump 64 will exhaust the chamber 16 sufficiently to reduce the chamber pressure to substantially zero atmospheric pressure. It should be understood that there is always some residual absolute pressure in the mixing chamber 16 but it is to be minimized as much as possible.

With the magnetic stirrer 20 and the digital display volt meter 54 operating, the first component of the gas mixture is introduced into the mixing chamber 16 by opening the appropriate inlet valve, such as 40a. During such filling of the chamber 16, operation of the vacuum pump may be interrupted but it is not necessary to do so. When the pressure of the first component reaches the desired level as indicated on the volt meter 54, the inlet valve is closed and the vacuum pump is used to purge the chamber 16 back to substantially zero atmospheric pressure. This operation is repeated with the first component gas until it is reasonably certain that the mixing chamber 16 is free from any other gases except the first component gas. Component gases are then individually introduced in the chamber to obtain predetermined pressure levels that will be more fully explained. Preferably, there will be a delay time in introducing the various components into the chamber in order to compensate for temperature variations caused by the expansion or contraction of the gases during the filling process. The relatively large mass of the pressure vessel V aids in stabilizing the temperature and enhancing the accuracy of the blending process.

For simplicity of operation, the percent by volume concentration of the component sample can be made equal to the absolute pressure per square inch value by having the total pressure of the reference sample in the mixing chamber 16 equal to 100 p.s.i. absolute. Such total sample pressure simplifies and reduces the chance of error in the following calculations.

The concentration of each gas component of the gas mixture is determined by the following known formula:

$$\% \text{ component by volume} = \frac{\text{component partial absolute pressure} \times 100}{\text{total absolute pressure}}$$

From the foregoing formula, the pressure required for each component addition may be determined by the following formula:

Required amount of pressure for the component =
Existing chamber pressure +
$$\frac{\% \text{ desired component concentration} \times \text{total pressure}}{100}$$

Where:

Component partial pressure equals difference in pressure (PSIA) before and after its introduction to the mixing chamber.

The total pressure is the final pressure (PSIA) obtained after all components have been introduced.

The required pressure is defined as the pressure (PSIA) level which must be obtained when introducing a component gas into the mixing chamber 16. It is equal to the existing chamber pressure plus the component partial pressure.

As noted previously, the percent volume concentration can be made equal to the PSIA by having total pressure of the reference sample made equal to 100 PSIA.

Using the foregoing formula, the various components of the gas mixture are introduced into the chamber 16 with the valves 72 and 68 closed. When preparation of the mixture is complete, it may be transferred by the branch connection 62 into a sample container which may be used to introduce the mixture directly into an analyzer or it may be stored for future use.

Preparation of a Mixture by Combined Partial Pressure and Addition of Specific Volume The initial procedure for purging the mixing chamber of undesired components is the same as that for the general partial pressure technique. A known volume of the desired low concentration component gases, vapors, or liquids are introduced at any suitable interval by means of a syringe and the septum inlet port. The major components are introduced by partial pressure technique at any suitable interval by means of the appropriate inlet valves 40a–40i. Low concentrations (part per million levels) of components can be achieved by injection of microliter quantities. These concentrations can be further reduced to the "parts per billion range" by dilution. This is accomplished by venting to reduce the mixing chamber pressure followed by repressurization with an appropriate dilution gas. Combinations of direct injection and dilution can produce component concentrations of any desired level.

Concentrations of each gas or vapor component of the mixture are determined by the following formula:

PPM by volume =
$$\frac{*\text{volume of gas or vapor added by syringe} \times 10^6}{\text{volume of mixing chamber}} \times \frac{\text{absolute chamber pressure}}{\text{atmospheric pressure}}$$

$$\text{vapor or gas volume in liters} = \frac{\text{liquid volume in mililiters} \times \text{specific gravity} \times 22.4}{\text{molecular weight}}$$

The following formula is used to calculate a new component concentration level following a dilution:

PPM component by volume after a dilution = initial concentration in PPM × $\frac{\text{absolute pressure after venting}}{\text{absolute pressure after repressurization}}$ Note that temperature corrections are not required when the mixing chamber and its contents are maintained at constant temperature during the blending process.

The foregoing disclosure and description of the present invention are illustrative and explanatory thereof and various changes in the size, shape and materials as well as in the details of the preferred embodiment may be made without departing from the spirit of the invention.

I claim:

1. Apparatus for producing a calibration gas mixture of known composition from a plurality of component gases separately introduced therein and blended together for use with analytical instrumentation, including:

a pressure vessel forming a gas mixing chamber of mass large relative to the mass of the gaseous contents introduced therein to provide a sufficient heat sink to hold the gas temperature substantially stable during the blending of the gases;

a stirring element movably disposed in said gas mixing chamber for homogenizing the mixture of gases introduced into, and retained within, said chamber while the gases are homogenized;

exhaust valve means operatively communicated with said chamber for controlling flow from said gas mixing chamber;

vacuum means communicating with said exhaust valve means of said gas mixing chamber for substantially exhausting said gas mixing chamber when desired;

pressure transducer means for measuring the absolute pressure of the gases in said mixing chamber and producing a usable output signal in response to the absolute pressure present in said mixing chamber;

pressure indicator means operatively connected with said pressure transducer means for displaying the absolute pressure measured by said pressure transducer means; and a plurality of inlet valves, each of which is in fluid communication with said mixing chamber and with a supply of a component gas of the gas mixture for controlling the introduction of the desired component gases into said mixing chamber.

2. The apparatus as set forth in claim 1, wherein said stirring element has magnetic properties;

a movable drive magnet disposed exteriorly of said pressure vessel and in such near proximity of the stirring element to effect a sufficient magnetic force between the drive magnet and the stirring element to effect movement of said stirring element when said drive magnet moves; and means operatively connected with said drive magnet for moving said drive magnet.

3. The apparatus as set forth in claim 2, wherein:
said means for moving said drive magnet is an electric motor.

4. The apparatus as set forth in claim 2, including:
said stirring element is rotatably mounted in said mixing chamber; and
said drive magnet is rotated to rotate said stirring element.

5. The apparatus as set forth in claim 4, wherein:
said means for rotating said drive magnet is an electric motor.

6. The apparatus as set forth in claim 1, wherein said vacuum means further includes:
a vacuum pump means for exhausting to an absolute pressure of substantially zero; and
vacuum conduit means for fluidly connecting said vacuum pump means and said exhaust valve means.

7. Apparatus for producing a calibration gas mixture of known composition for use with analytical instrumentation, including:
a pressure vessel forming a gas mixing chamber;
mixing means for homogenizing the mixture of gases introduced into said chamber;
vacuum means communicating with said gas mixing chamber for substantially exhausting said gas mixing chamber when desired;
pressure transducer means for measuring the absolute pressure of the gases in said mixing chamber and producing a usable output signal in response to the absolute pressure present in said mixing chamber;
pressure indicator means operably connected with said pressure transducer means for displaying the absolute pressure measured by said pressure transducer means;
a plurality of inlet valves, each of which is in fluid communication with said mixing chamber and with a supply of a component gas of the gas mixture for controlling the introduction of the desired component gases into said mixing chamber;
a vacuum pump means for exhausting to an absolute pressure of substantially zero;
exhaust valve means for controlling flow from said mixing chamber to said vacuum pump means;
vacuum conduit means for fluidly connecting said vacuum pump means and said exhaust valve means;
a branch connection means for forming a passageway for transferring the mixture of gases in said mixing chamber into a sample container; and
a sample valve in said branch connection for controlling flow through said branch connection.

8. The apparatus as set forth in claim 1, wherein:
said pressure transducer is one producing a direct current or voltage output signal that increases linearly with increased pressure in the mixing chamber; and
said pressure indicator means is one having a digital display of the voltage output signal of the pressure in said mixing chamber.

9. The apparatus as set forth in claim 1, wherein:
each of said inlet valves is a right angled type valve mounted with the pressure vessel.

* * * * *